United States Patent [19]

Glazer et al.

[11] Patent Number: 5,565,554
[45] Date of Patent: Oct. 15, 1996

[54] DIMERIC FLUORESCENT ENERGY TRANSFER DYES COMPRISING ASYMMETRIC CYANINE AZOLE-INDOLENINE CHROMOPHORES

[75] Inventors: Alexander N. Glazer, Orinda; Scott C. Benson, Albany, both of Calif.

[73] Assignee: The Regents of the University of California, Oakland, Calif.

[21] Appl. No.: 283,006

[22] Filed: Jul. 29, 1994

[51] Int. Cl.$^6$ .......................... C07H 19/00; C07D 221/12
[52] U.S. Cl. ............................................ 536/26.6; 546/107
[58] Field of Search .......................... 536/26.6; 546/108, 546/109, 176

[56] References Cited

U.S. PATENT DOCUMENTS 5,312,921  3/1994  Glazer et al. ............................ 546/108

OTHER PUBLICATIONS

Rye et al, W. Cleic, Acid. Res 20: 2803–2812 (1992).
Benson et al., Nucleic Acids Research (1993) 21:5720–5726.
Hamer, "The Cyanine Dyes in Related Compounds," in The Chemistry of Heterocyclic Compounds, vol. 18, pp. 210–239 (Interscience Publishers, New York, 1964).
Ernst et al., Cytometry (1989) 10: 3–10.

*Primary Examiner*—Stephanie W. Zitomer
*Assistant Examiner*—Eggerton Campbell
*Attorney, Agent, or Firm*—Bertram I. Rowland

[57] ABSTRACT

Novel fluorescent DNA-staining dyes are provided combining asymmetric cyanine azole-indolenine dyes, which provide for strong DNA affinity, large Stokes shifts and emission in the red region of the spectrum. The dyes find particular application in gel electrophoresis and for labels which may be bound to a variety of compositions in a variety of contexts.

12 Claims, 3 Drawing Sheets

DIMERIC FLUORESCENT ENERGY TRANSFER DYES COMPRISING ASYMMETRIC CYANINE AZOLE-INDOLENINE CHROMOPHORES

This invention was made with Government support under Grant (Contract) No. DE-G-91ER61125 awarded by the Department of Energy. The Government has certain rights to this invention.

TECHNICAL FIELD

The field of this invention is DNA fluorescent stains.

BACKGROUND

Detection of fluorescent signals finds wide applications in a variety of situations and under a variety of conditions. Fluorescence has many advantages as a means of generating a detectable signal. Fluorescence does not suffer from the many disadvantages of a radioactive label, while in many cases it provides for a high level of sensitivity.

There is substantial interest in being able to obtain fluorescence at longer wavelengths, where there is less interference from light resulting from scattering from components in the medium being irradiated. By providing for combinations of dyes with long Stokes shifts, one can achieve high sensitivity fluorescence detection of DNA, where the dye becomes bound to DNA and provides for a shift in the spectral properties of the resulting dimer.

RELEVANT LITERATURE

Co-pending application, Ser. Nos. 08/161,231; 08/009,704 now U.S. Pat. No. 5,401,847; 08/060,910 now U.S. Pat. No. 5,312,921; and 08/189,924 describe monomeric and dimeric dyes for binding to DNA finding application in gel electrophoresis and as labels in a variety of contexts. U.S. Pat. No. 5,312,921 provides for a number of different homodimeric and heterodimeric dyes which bind to DNA. The stability of dsDNA-dye complexes is described by Benson et al. (1993) *Nucleic Acids Res.* 21, 5720–5726, Carbocyanine dyes are described by Hamer, "The Cyanine Dyes in Related Compounds." In *The Chemistry of Heterocyclic Compounds*. Vol. 18, pages 210 and 239, Interscience Publishers, NY, 1964. Synthesis and application of azole-indolenine dicarbocyanine dyes for use as covalent labels are described in Ernst et al., (1989), *Cytometry* 10,. 3–10.

SUMMARY OF THE INVENTION

Figure 1:
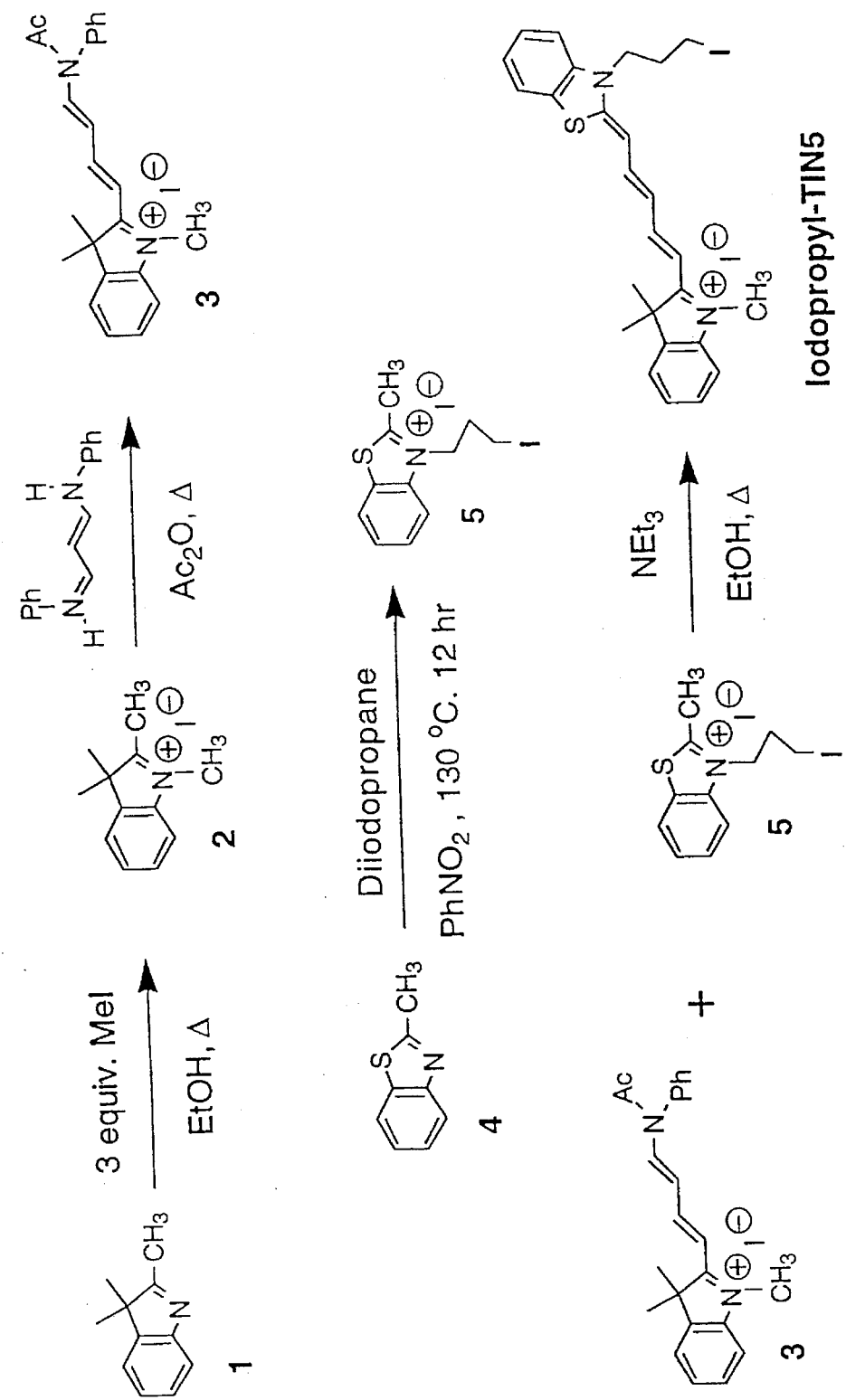
FIG. 1 (Scheme 1) is the synthetic scheme for the preparation of N-iodopropyl-TIN-5 2-[5'-(3"iodopropyl-(benzo-1",3"-thiazole)-2"-ylidene)- 1',3'-pentadienyl]-methyl-3,3-dimethylindoleninium iodide.

Novel heterodimeric fluorescent asymmetric carbocyanine dyes are provided for binding to DNA to serve as fluorescent stains. The dyes have a strong affinity for DNA and can be used in get electrophoresis for extended periods of time, even with small DNA molecules. The dyes provide for absorption at convenient wavelengths below about 500 nm ($\epsilon$>40,000) with strong emission at wavelengths above 650 nm to substantially diminish background, as well as contributions from dyes emitting at shorter wavelengths where two or more dyes are used in multiplex applications..

DESCRIPTION OF SPECIFIC EMBODIMENTS

Novel compositions and their use are provided, where the compositions comprise fluorescent asymmetric dicarbocyanine azole-indolenine dyes, their complexes with DNA, and their use in gel electrophoresis and as labels for labeling a wide variety of materials in various contexts.

The subject dyes may be divided into three parts: the carbocyanine azole dye, the carbocyanine azole-indolenine dye; and the linking group. The asymmetric carbocyanine azole dyes have been extensively described in the literature, as well as their preparation. The cyanine dye structures contain two end groups with a positive charge in conjugation through a linking methine chain, the asymmetric cyanine dyes are unique in having two different groups. The linking methine chain may contain from about 1 to 9 carbon atoms in the chain and may be part of an alicyclic or aromatic ring, and may be substituted with alkyl or heteroatom functional groups. The asymmetric azole carbocyanine dye will normally have one benzazole end group with two heteroatoms, at least one of which will be nitrogen, the other will be nitrogen, oxygen, sulfur, or selenium, where the heteroatoms will be in the one, three-positions of the azole ring. The second end group of the azole dye will normally have an aromatic ring containing at least one heteroatom, usually nitrogen, sulfur or oxygen. The asymmetric azole-indolenine carbocyanine dye will have an indolenine end group normally containing one heteroatom, including nitrogen, sulfur, oxygen or selenium, usually nitrogen. The indolenine carbocyanine will also have an azole end group, having a second heteroatom, which may be oxygen, sulfur, nitrogen or selenium.

The azole-indolenine dye will be linked to the azole dye through a hydrocarbyleneaminohydrocarbylene group of from 4 to 30, usually of from 4 to 16 carbon atoms, of from 2 to 6 hydrocarbylene groups, where the groups may be aliphatic, alicyclic or aromatic, particularly alkyleneaminealkylene linkages of from 2 to 6, usually 2 to 5, alkylene groups, particularly where at least one of the amino groups is tetrasubstituted, usually with two alkyl groups of from one to three carbon atoms, usually one to two carbon atoms, there usually being from one to five, more usually one to three alkyleneamino groups, followed by an alkylene group, where the alkylene groups will be of from two to four, usually two to three carbon atoms.

The subject compositions would generally have from about 40 to 80 carbon atoms, more usually from about 45 to 60 carbon atoms, and from 7 to 12 heteroatoms, primarily nitrogen and sulfur, although oxygen, selenium and other heteroatoms may also be present. The linking group will generally be of at least five atoms other than hydrogen, and not more than about 30 atoms other than hydrogen, usually having from about five to 15 atoms in the chain and from one to five nitrogen atoms, where one or more of the nitrogen atoms may be quaternary, preferably all of the nitrogen atoms being quaternary.

Compounds of this invention will have the following formula:

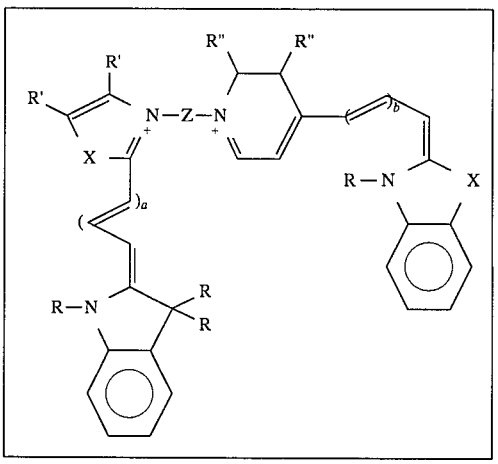

wherein:

a is from 0 to 6, usually 1 to 5, wherein the carbon atoms of the double bonds may be substituted or unsubstituted, there usually being not more than one substituent per double bond, where the substituents may have from 0 to 6, usually 0 to 3 carbon atoms and 0 to 4, usually 0 to 3 heteroatoms, which will usualy include oxygen, sulfur, nitrogen and halogen, as illustrated by alkyl of from 1 to 6 carbon atoms, cyano, oxy of from 0 to 6 carbon atoms, carbonyl, both oxo and non-oxo of from 1 to 6 carbon atoms, amino and substituted amino of from 0 to 6 carbon atoms, nitro, thio of from 0 to 6 carbon atoms, imino, combinations thereof, and the substituents may be taken together to from an aromatic or alicyclic ring of from 5 to 7 annular members, e.g. butadienylene and butylene;

b is from 0 to 4, usually 0 to 3, wherein the carbon atoms of the double bonds may be substituted or unsubstituted, there usually being not more than one substituent per double bond, where the substituents may have from 0 to 6, usually 0 to 3 carbon atoms and 0 to 4, usually 0 to 3 heteroatoms, which will usually include oxygen, sulfur, nitrogen and halogen, as illustrated by alkyl of from 1 to 6 carbon atoms, cyano, oxy of from 0 to 6 carbon atoms, carbonyl, both oxo and non-oxo of from 1 to 6 carbon atoms, amino and substituted amino of from 0 to 6 carbon atoms, nitro, thio of from 0 to 6 carbon atoms, imino, combinations thereof, and the substituents may be taken together to from an aromatic or alicyclic ring of from 5 to 7 annular members, e.g. butadienylene and butylene;

each of the R groups are the same or different, R is alkyl of from 1 to 3 carbon atoms or substituted alkyl of from 1 to 12 carbon atoms and 1 to 2 heteroatoms, which are oxygen, nitrogen, sulfur, phosphorous, boron, lathanide, or other organometallic substituent;

each of the R' groups are the same or different, wherein when other than hydrogen, R' is aliphatic, alicyclic, heterocyclic or aromatic of from 1 to 12 carbon atoms and from 0 to 2 heteroatoms including nitrogen, oxygen, sulfur or selenium, and may be taken together to define an aromatic ring fused to the ring to which the R' groups are attached, the ring being of from 5 to 6 members, usually 6 members, particularly carbocyclic;

each of the R" groups are the same or different, and come within the definition of R', except that two RΔ groups may be taken together to define a double bond;

X may be a heteroatom or carbon atom, wherein the heteroatom may be nitrogen, oxygen, sulfur or selenium and the carbon atom is dialkyl substituted, where the alkyl group may be of from 1 to 12, usually 1 to 3, carbon atoms and from 0 to 3 heteroatoms, including nitrogen, oxygen, sulfur or selenium; and Z is a linking group comprising hydrocarbyleneaminohydrocarbylene, having from 1 to 5 amino groups, where one of more of the nitrogen atoms may be replaced with boron, lanthanide, or other metal cation, wherein the hydrocarbylene groups may be aliphatic alicyclic or aromatic of from 2 to 12, usually 2 to 8 carbon atoms, and the nitrogen atoms are secondary, tertiary or quaternary, with N-alkyl substituents of from 1 to 6 carbon atoms;

wherein the aromatic rings may have a total of from 0 to 4 substituents of from 1 to 6 carbon atoms and 0 to 4 heteroatoms each, wherein the heteroatoms are oxygen, nitrogen and sulfur, providing for such groups as oxy, carbonyl, oxo and non-oxo, amino, nitro, thio, cyano, imino, and comnbinations thereof.

Various counterions may be employed as the anions for the positive charges of the dye. Conveniently, iodide finds use, although other halogens or other anions may find application in particular situations.

Substituents may include methyl, ethyl, propyl, hydroxyethyl, methoxypropyl, ethylthioethyl, cyanoethyl, phenyl, anisyl, ethoxycarbonylethyl, nitrophenyl, 4-aminobutyl, cyclopentyl, 2-furyl, 5-methylthiophenyl-2, ferrocenyl, lanthanyl chelate, phosphate, phosphoramidate, dimethoxyboryl, and butylselenyl.

Compounds coming within the scope of this invention include heterodimers composed of oxazole yellow, thiazole orange, thiazole blue, indolenine-azole, and indolenine-quinoline cyaninees linked to indolenine-thiazole, indolenine-oxazole, and indolenine-selenazole carbocyanines.

Compounds of interest include 1-[1"-[4'-[3"-methyl-2", 3"-dihydro-(benzo-1",3"-thiazole)-2"-ylidene]-methyl-pyridiniumiodide]]-11-[3'-[2'[5'-1'"-methyl-3'",3'"-diethylindolenine-2'"-ylidene)- 1",3"-[pentadien-1"-yl]-benzo-1'3'-thiazolium iodide]]-4,4,7,7-tetramethyl-4,7-diazaundecamethylene diiodide; 1-[1'-[4'-[3"-methyl-2",3"-dihydro-(benzo-1",3"-thiazole)-2"-ylidene]-methyl-quinoliniumiodide}]-11-[3'-[2'-[5'-1'"-methyl-3'",3'"-dimethylindolenine-2'"-ylidene)-1'",3"-[pentadien-1"-yl]-benzo-1'3'-oxazolium iodide]]-4,4,7,7-tetramethyl-4,7-diazaundecamethylene diiodide; 1-[1'-[4'-[3"-butyl-2",3"-dihydro-(benzo-1",3"-diazole)-2"-ylidene]-methylquinolinium iodide]]-11-[3'-[2'-[5'-1'"-methyl-3'",3'"-diethylindolenine-2'"-ylidene)- 1",3"-[pentadien-1"-yl]-benzo-1'3'-thiazolium iodide]]-4,4,7,7-tetramethyl- 4,7-diazaundecamethylenediiodide;1-[1'-[4'-[3"methyl-2",3"-dihydro-(benzo-1",3"-thiazole)-2"-ylidene]-methyl-quinolinium iodide]]-11-[3'-[2'-[5'-1'"-methyl-3'",3'"-dimethylindolenine-2'"-ylidene)-1",3"-[pentadien-1"-yl]-benzo-1'3'-thiazolium iodide]]-4,4,7,7-tetramethyl-4,7-diazaundecamethylene diiodide; 1-[1'-[4'-[3"-methyl-2",3"-dihydro-(5"-chlorobenzo-1", 3"-thiazole)-2"-ylidene]-methyl-quinoliniumiodide]]-11-[3'-[2'-[5'-1'"-ethoxyethyl-3'",3'"-dipropylindolenine-2'"-ylidene)-1",3"-[pentadien-1"-yl]-benzo-1'3'-thiazolium iodide]]-4,4,7,7-tetraethyl-4,7-diazaundecamethylene diiodide; and 1-[1'-[4'-[3"-methyl-2",3"-dihydro- 1",3"-thiazole)-2"-ylidene]-methyl-pyridiniumiodide]]-11-[3'-[2'-[5'-1'"-methyl-3'",3'"- dimethylindolenine-2'''-ylidene )-1",3",5"-[heptatrien-1"-yl]-benzo-1'3'-thiazolium iodide]]-4,4,7,7-tetramethyl-4,7-diazaundecamethylene diiodide.

The subject compounds will have an affinity for dsDNA of at least about $5 \times 10^6$ $M^{-1}$, more usually at least about $10^7$ and greater than about $10^9$ $M^{-1}$ at ionic strengths of at least about 0.01, usually at least about 0.04, preferably at least about 0.2° at 25° C. Gel electrophoresis is usually performed at an ionic strength of about 0.04.

These compounds find use as labeling agents, where the compounds are used in a process for detection of nucleic acid or as a label which is prepared for labeling a compound to provide a fluorescent signal.

The first situation is exemplified by separations employing an electrical field, e.g. electrophoresis. In employing the subject compounds, the nucleic acid, usually dsDNA, and the dye may be brought together in an appropriately buffered medium and incubated for sufficient time for the dye to non-covalently bind and intercalate in the nucleic acid for prestaining. The ratio of dye to ds nucleic acid may be varied widely ranging from about one molecule of dye per four base pairs, to as little as one molecule of dye per 200 base pairs, usually ranging from about one dye molecule per 4 to 100 base pairs, depending upon the desired degree of sensitivity, size and nature of the nucleic acid molecule, choice of dye, manner of measuring, period of time for the electrophoresis, and the like. Dye present in excess of one dye per four base pairs, or more, does not significantly influence the observed signal, so that any increase in the amount of dye above a mole ratio of one dye molecule per four base pairs will normally be undesirable. Generally, the amount of dye will range from about one molecule per 4 to 50 base pairs for optimum results. It is important that large excesses of dye to nucleic acid basse pairs and high concentrations of nucleic acid be avoided, as this can lead to precipitation of the nucleic acid, particularly when applying the sample to the gel.

The subject dyes may be used in electrophoresis, with dsDNA having as few as about 70 bp, with no upper limit. The time for the gel electrophoresis with prestained dsDNA will vary inversely proportional to the smaller size of dsDNA to be detected, where the time will generally be in the range of about 2 to 60 min, the longer times being associated with the larger DNA being the minimum DNA to be detected.

The amount of nucleic acid will generally be conventional amounts employed for electrophoresis, generally ranging from about 0.005 ng/µl to 5 ng/µl. Various conventional buffers may be employed, such as Trisacetate or Tris-borate, generally present in the range of about 1 to 50 mM, more usually in the range of about 1–20 mM, to provide a pH in the range of about 5 to 10, more usually about 7 to 9. Also, a metal ion chelator may be present in minor amount, generally from about 0.05 to 0.5 mM. Conveniently, EDTA may be employed.

The dye and nucleic acid may be incubated, usually for at least 5 minutes and not more than about 2 hours, where complex formation will normally be complete in less than about one hour, usually in about 30 min. at room temperature. The incubated solution may be used directly or further diluted, as appropriate, prior to application to the gel.

Tracking dyes are preferably not used, since it is found that the tracking dyes may tend to interfere with the detection of the non-covalently bound and intercalated dye. Also, gels may be subjected to pre-electrophoresis for sufficient time to decrease background fluorescence, usually not more than about three hours.

The electrophoresis may be performed in any convenient and conventional manner, where the bands may now be detected by fluorescence of the non-covalently bound and intercalated dye. The electrophoresis insures that unbound dye is removed from the region of the bands and the dye is found to be retained by the nucleic acid, so that individual bands may readily be detected by fluorescence scanning. The irradiation and detection system will be directed to excitation in the range of about 450–500 nm and detection in the range of about 650–700 nm. Thus, a convenient laser can be employed, such as an argon laser which provides for coherent light at 488 nm. When using thiazole orange as the absorbing moiety, the excitation light wavelength will be at or about 485–490 nm.

Of particular interest is the use of a confocal laser scanning fluorescence imaging system. A system which has been found to be convenient employs a long pass dichroic beam splitter to reflect the laser beam down through a microscope objective and onto the sample. The fluorescence emission is collected by the objective and passed through the beam splitter to a photodetector. The fluorescence emission is then passed through a spatial filter to effect confocal detection and a long pass or bandpass color or interference filter before reaching a photomultiplier tube. An appropriate servo motor-driven XY translation stage is employed with a 2.5 µm resolution to translate the gel past the laser beam at a convenient speed, generally about 1–5 cm/sec. A microcomputer may be employed to control the XY translation stage and to acquire and display images. The fluorescence images may then be pseudo-color encoded to represent different intensity levels and contrast stretched with a histogram equalization method to enhance the images. To quantitate the image data, the image columns that enclose the nucleic acid bands may be extracted and integrated.

The nucleic acid may be readily isolated free of the intercalated fluorescent dye for further use. One may use the Geneclean® kit for recovery of 50% or better of the nucleic acid. By combining the intercalated dye containing nucleic acid with Glassmilk in an aqueous solution of alkali metal iodide, e.g. 1–10 ng nucleic acid (1–5 µg/ml nucleic acid) and about 1–10µg/ml of Glassmilk, incubating with agitation for about 5–60 mins. followed by centrifugation, the resulting pellet in an appropriate ethanolic buffered aqueous solution (e.g. 1:1) followed by centrifugation and repeating this washing procedure, the nucleic acid is obtained substantially free of the fluorescent dye.

By virtue of the use of the subject binding fluorescent dyes in the electrophoresis, greatly enhanced sensitivities are achieved due to the much higher level of fluorescence intensity which is obtained. Sizes and amounts of DNA fragments in mixtures of unknown composition can be determined with a total amount of material ranging from 100 µg to 1 ng depending on the complexity of the mixture and the size range of the fragments. Thus, the subject method can find application in the detection of nucleic acid of less than about 5 ng, particularly less than about 1 ng, frequently less than about 100 pg, even less than about 50 pg.

Instead of employing the subject dyes for detection of nucleic acid bands in electrophoresis, compositions comprising dsDNA and the subject dyes at substantial saturation may be employed, where the dsDNA is joined to an entity for binding to another entity, either covalently or non-covalently. The entities will be either referred to as specific binding pairs, since the entities will have specific affinity for a complementary entity, as compared to diverse other types of molecules, or covalently binding functionalities for reacting with other molecules, such as polypeptides or saccharides.

The specific binding pairs may involve a wide variety of molecules, which are arbitrarily called ligands and receptors. For the subject invention, the ligands and receptors may include a wide variety of proteins, such as antibodies, specific binding proteins, such as surface membrane protein receptors, lectins, blood proteins, and the like, carbohydrates, small organic molecules, both naturally occurring and synthetic to which proteins specifically bind, either naturally occurring protein receptors or antibodies, nucleic acids which may hybridize or specifically bind to an homologous or partially homologous sequence usually having at least about 30% complementarity, preferably at least about 50% complementarity over the complementary region, and the like. In effect, any two molecules which have a specific binding affinity may be employed, so that the label may be used for detection of the presence of the complementary member. The desired specificity may be varied widely, depending upon the particular nature of the molecules to be detected, the information desired about the nature of the sample, or the like.

The labels may be used for detecting any of a wide variety of molecules in a wide variety of samples, which includes physiological samples, e.g. blood, plasma, urine, spinal fluid, saliva, feces, mucus, etc., waste samples, from processing, garbage, soil, water, etc., contaminants in products, such as food, drugs, etc.

Depending upon the fluorescence intensity one desires, one can vary the length of the dsDNA and the level of non-covalent binding and intercalation to increase the fluorescence intensity per molecule. Usually, there will be at least about 16 base pairs, more usually at least 20 base pairs, and one may have dsDNA of at least about 1 kbp or even 2 kbp or more. The particular length of the dsDNA is not critical to this invention and may be varied in accordance with the fluorescence intensity desired per molecule, purpose of the label, convenience, and the like. With some dyes there can be an increase in fluorescence intensity by having A-T pairs. Thus, one may provide for a poly A-T.poly A-T dimer to be used as the label. However, if one wishes to further increase the stability of the dsDNA, beyond that which the intercalating dimer provides, one can use a combination of AT and GC pairs or a poly G-C.poly G-C dsDNA. Alternatively, one may use any source of random DNA, such as calf thymus DNA, $E.$ $coil$ DNA, etc.

The dsDNA should provide for means for binding to another molecule. This can be achieved in a wide variety of ways, depending upon the manner in which the label is to be employed. For example, the dsDNA may include biotin conjugated nucleotides, one or more biotins, where the biotin will bind to avidin or streptavidin (hereafter both will be referred to as "avidin"). The biotins may vary from one biotin per nucleotide to 0.1% of the nucleotides depending on the nature of the procedures, conditions, etc. Alternatively, any molecule may be employed, particularly a small organic molecule (less than about 2 kdal) which is unlikely to be encountered in the sample of interest, where the small organic molecule has a specific receptor or antibody, particularly monoclonal antibody, to which it specifically binds. Thus, thyroxine, corticosteroids, estrogens, retinoic acid, mannose and the like may be used with proteins which bind specifically to such molecules. Alternatively, synthetic or naturally occurring molecules may be employed for which antibodies have been produced, such as 2,4-dinitrophenyl, barbiturate, phosphatidylcholine, digoxigenin, etc. These molecules may be included during synthesis of the DNA by being linked to an internal or terminal nucleotide, where the DNA is synthesized in accordance with conventional automatic procedures, or may be added after synthesis of the DNA by linking either available hydroxyl or amino groups.

The binding entity may be an active functionality for covalently bonding to a molecule having a functionality capable of forming a stable covalent link, such as amino, hydroxyl, thio, carboxyl, activated olefin or aryl, or the like where the functionality to other than a naturally occurring functionality of the nucleotide. The label may be modified with an activated olefin, such as maleyl, for reaction with a thiol group, a carboxyl for reaction with an amine, or the like. In this manner, many different types of molecules may be fluorescently labeled for use in diagnostics, both competitive assays and non-competitive assays, histology, cytology, separations e.g. electrophoresis, HPLC, FACS, and the like.

The strands of DNA may take various structures. In many situations, the dsDNA may comprise two strands, where the strands may be completely or only partially overlapping, where the ends may extend in the 5' and/or 3'directions, so that one strand may be substantially longer than the other strand, where the other strand may bind either 5' proximal, 3'proximal or centrally. Alternatively, the two strands may overlap to provide for staggered ends, where the single stranded portions of the DNA may then be used to bind to complementary sequences. Alternatively, one may provide a single strand with an inverted repeat, so that the strand loops back on itself to provide the double stranded portion. The hairpin structure may be used solely for labeling, or a single stranded portion of the hairpin may be employed for hybridizing to a complementary sequence. The hybridizing single stranded portion may be an extension at either the 5' or 3'end to provide for a staggered terminus or may be present in the loop of the hairpin.

The subject labels may be used in a wide variety of environments and contexts to provide for high levels of fluorescence intensity without interference from the molecules to which the labels bind, either directly or indirectly, the media employed, the conditions employed, and the like. Thus, the subject labels may be employed in specific binding pair assays, where the label may be readily linked to another molecule through a specific binding pair combination. For example, in diagnostic assays, one may combine an avidin conjugated antibody, where the antibody binds to a molecule of interest, to biotin labeled DNA dye aggregate to provide for fluorescent labeled antibody.

Alternatively, the antibody may be labeled with biotin, so that avidin may act as a bridge between the biotin labeled antibody and the biotin labeled DNA dye aggregate. In this way, the fluorescent label may be added after combining the sample with a complementary specific binding pair member and carrying out the assay, followed by addition of label and removal of any nonspecifically bound label.

Where a single stranded DNA sequence is provided as part of the label, this can be used for hybridizing to complementary DNA or RNA sequences. The presence of the non-covalently bound and intercalated dye greatly enhances the stability of the dsDNA. Thus, one can introduce the subject labels into a denaturation medium under conditions where the non-covalently bound and intercalated dsDNA will be stable, while the sample DNA may be denatured to provide for single strands. Where single stranded DNA or RNA is present, there will be no need for providing for denaturation conditions. Therefore, the subject molecules may be used as probes to identify DNA sequences under a wide variety of conditions, including electrophoresis, polymerase chain reactions, where the single stranded sequence may serve as a primer, in Southern blotting, Northern blotting and the like.

Instead of having non-covalent complexes between the non-nucleic acid specific binding pair member and the DNA dye aggregate, one can provide for covalent bonding. Thus, by providing for activated groups such as carboxy, diazo, activated ethylene, or the like, the fluorescent moiety may be readily linked to other molecules, such as proteins, sugars, lipids, or the like by employing conventional linking groups resulting in amide, amines, diazo, esters, thioethers, and the like. For example, one may introduce a thiol group at either the 3' or 5' terminus of a synthetic oligonucleotide, synthesize the complementary strand and form a non-covalently bound and intercalated dye complex. The thiol group on the DNA can then be reacted with a maleimide modified protein, e.g. an antibody. Other techniques may follow conventional procedures found in the literature.

One may also use the subject labels in a fluorescence activated cell sorter to provide for greatly enhanced sensitivity as a result of the substantially increased fluorescence intensity. Again, one may use ligands for surface membrane receptor proteins, sugars for lectins, antibodies for epitopes present on the surface of the cell, or the like, where the subject labels may be bound covalently or non-covalently to the molecule which binds to the cell component.

With the subject compositions one can also detect proteins to transcriptional initiation elements, e.g. promoters, operators, enhancers, etc. By having labeled dsDNA, according to the subject invention, mixed with labeled proteins, labeled with a fluorescent molecule emitting at a different wavelength from the non-covalently bound and intercalated fluorescer, or other appropriate label, one can determine the presence of transcription factors and cofactors. For example, one can gel electrophorese the mixture and identify the presence of the protein bound to DNA by virtue of the double labelling.

One may also use the subject fluorescent non-covalently bound and intercalated DNA for in situ hybridization studies, intermolecular transfer of fluorescent molecules from one doubly stranded nucleic acid molecule to another, e.g. for transferring fluorescent dye without the fluorescer being transferred to the medium. This may find use in making chromosomes with triplex formation, in transferring to nucleic acid in a gel or on a membrane, etc. The fluorescer intercalated DNA may be bound to a particle, e.g. magnetic, to be removed after use as transfer agent.

The subject labels may be used with advantage with a confocal fluorescence imaging system, as described previously. With the subject compounds, substantially less than 100 pg of DNA can be detected, usually less than about 50 pg, but more than about 10 pg.

In histology and cytology the subject fluorescent labels provide for high sensitivity in detecting target epitopes, particularly at low levels.

The subject compositions may be synthesized in accordance with conventional techniques. See, for example, Glauert and Mannn (1952) *J. Chem. Soc.* 5012; Brooker et al. (1942) *J. Am. Chem. Soc.* 64, 199–210; Brooker et al. (1941) (1941) *ibid* 63, 3192–3203; Rye et al. (1992) *Nucleic Acids Res.* 20, 2803–2812. Particularly, the activated methyl groups of N-substituted methylindolinium and methylbenothiazole, may be linked through carbylene groups to various end groups to form the asymmetric cyanine dyes by displacement of anil groups. The carbocyanine azole-indolenine dye can be linked to a cyanine, xanthine, rhodamine, phenoxazine or other dye through a hydrocarbyleneaminohydrocarbylene group by a variety of approaches, conveniently by substituting one of the dye moieties with a hydrocarbyleneamino or polyhydrocarbyleneamino group and linking the other dye moiety through a haloalkyl group.

The following examples are offered by way of illustration and not by way of limitation.

EXPERIMENTAL

Materials and Methods 2,3,3-Trimethyl indolenine, methylbenzothiazole, iodomethane, and diidopropane were purchased from Aldrich and used without further purification. Malonaldehyde dianil was synthesized according to literature reports (Glauert, R. H. and Mann, F. G. *J. Chem. Soc.* (1952) 5012, by the method of Claisen Ber. (1903) 36, 3668). Dry nitrobenzene was freshly distilled from $CaH_2$. Dry triethylamine was distilled from $Na°$. DMF was predried with $MgSO_4$, fractionally distilled and stored over molecular sieves. All dry solvents were stored under $N_2$. All reactions were run under anhydrous conditions under $N_2$. Reactions were monitored by TLC (silica gel 60, $A_{260}$, Fisher) and visualized with short and long wavelength UV irradiation. Flash column chromatography was performed on silica gel 60 (200–440 mesh Fluka).

Synthesis

Scheme 1 (FIG. 1) outlines the synthesis of iodopropyl-TIN-5. 2,3,3,-Trimethylindolenine (1) reacted with 3 equivalents of iodomethane in refluxing anhydrous ethanol to produce 2 in 90% yield. Compound 2 reacted with 1.1 equivalent of malonaldehyde dianil in refluxing $AC_2O$ to produce a quantitative yield of compound 3. Methyl benzothiazole (4) was alkylated with 3 equivalents of diiodopropane in dry nitrobenzene overnight at 140° C. to give 5 in 87% yield. Compounds 3 and 5 reacted with mild heating in the presence of 2 equivalents of triethylamine to produce iodopropyl-TIN-5 2-[5'-(3"-iodopropyl(benzo-1",3"-thiazole)-2"-ylidene)-1',3'-pentadien-1'-yl]-methyl-3,3-dimethylindoleninium iodide. Iodopropyl-TIN-5 was purified by flash chromatography eluting with methanol/$CH_2Cl_2$ (1:20 v/v). The pure iodopropyl-TIN-5 was recrystallized from methanol:$CH_2Cl_2$(1:10 v/v)/ether to give TIN-5 in a 73% yield as a deep blue powder.

Scheme 2 (FIG. 2) outlines the synthesis of the TOTIN-5 heterodimer by the reaction of (tetramethylpropanediamino-)propyl thiazole orange, TO(6), described previously (Benson, S. C., Singh, P., and Glazer, A. N. (1993) *Nucleic Acids Res.* 21, 5727–5735), and 1.2 equivalents of iodopropyl-TIN-5 in anhydrous dimethylformamide. After 16–24 hours at 90° C., the crude product was precipitated from the reaction mixture with ether/petroleum ether and purified by flash chromatography employing EtOAc: AcOH: $H_2O$:$NEt_3$ (1:2:2:0.2). The pure product was recrystallized from methanol:$CH_2Cl_2$(1:10 v/v)/ether to give a 73% yield of TOTIN-5,1-[1'-[4'-[3"-methyl-2",3"-dihydro-(benzo-1",3"-thiazole)-2"-ylidene]-methyl-quinolinium iodide]]-11-[3'-[2'-[5'-1'''-methyl-3''',3'''-dimethylindolenine-2'''-ylidene]-1'',3''-[pentadien-1''-yl]-benzo-1'3'-thiazolium iodide]]-4,4,7,7-tetramethyl-4,4,7,7-diazaundecamethylene diiodide. No monomeric starting material was detected in the purified TOTIN-5 by thin layer chromatography with EtOAc: AcOH: $H_2O$ (1:2:2 v/v) or methanol:$CH_2Cl_2$/(1:10 v/v). The electrospray mass spectrum (skimmer voltage=40 V) of TOTIN-5 had major fragment peaks resulting from cleavage of the tetramethyldiaminopropyl linker to produce intact thiazole orange ($C_{26}H_{34}N_3S+$=376) and TIN-5 ($C_{26}H_{34}N_3S+$=444) singly charged cations with dimethylpropyl side chains.

Absorption Spectra of Iodopropyl-TIN-5 and TOTIN-5

Pure recrystallized iodopropyl-TIN-5 (4.7 mg, mw=654) was dissolved in 50 ml MeOH to give a stock solution [$1.47 \times 10^{-4}$ M]. A molar extinction coefficient of 230,200 at $\lambda_{max}$=643 nm was determined on a diluted sample (1/50) in MeOH. The solvent dependence of the absorption spectrum of TIN-5 was determined by running equal aliquots of the stock solution in MeOH, 4 mM Tris acetate-0.1 mM ethylenediamine tetraacetate buffer, pH 8.2 (TAE), or buffer plus calf thymus dsDNA at 20 base pairs (bp):dye, see Table 1.

The 450 to 550 nm region of the absorption spectrum of the TOTIN-5 heterodimer was closely matched by addition of the absorption spectra of the two monomers run at equimolar concentrations (FIG. 3). Therefore, the molar extinction coefficient TOTIN-5 in MeOH ($\lambda_{max}$ abs=507 nm, $\epsilon$79,000) was calculation from the known extinction coefficients of TO (6) (Benson, S. C., Mathies, R. A., and Glazer, A. N. (1993) *Nucleic Acids Res.* 21, 5720–5726), and iodopropyl-TIN-5 at 507 nm. The solvent dependence of the absorption spectrum of TOTIN-5 was determined as for the TIN5 monomer (Table 1).

Fluorescence Emission Spectrum of TOTIN-5 Determined Under Different Conditions The calf thymus DNA:TOTIN-5 complex was formed at 1 dye:100 bp DNA. In this complex, TOTIN-5 showed a 36 fold enhancement of 672 nm fluorescence emission (for 488 nm excitation) relative to that of the free dye (4 mM TAE, pH=8.2, $\lambda_{max}$ em (free)=665 nm). The intensity of TIN-5 emission at $\lambda_{max}$ em=672 nm per mole of dsDNA bound TOTIN-5 was found to be nearly constant for dye bound from 100 to 5 bp:dye.

At 488 nm, there is negligible direct excitation of the TIN-5 chromophore; virtually all of the energy is absorbed by the thiazole orange chromophore. At this low saturation of binding sites, the observed energy transfer from TO to TIN-5 originates within a dimeric molecule. The comparison of the relative emissions at 532 nm (TO) and 672 nm (TIN-5) established that such transfer is indeed very efficient. Under these conditions, the ratio of thiazole orange donor emission at 532 nm to TIN-5 acceptor emission at 672 nm is 1:2.7. As the ratio of dye to DNA bp increased to 1:5, quenching of the TO emission at 532 nm increased to >98% and the ratio of donor to acceptor emission decreased to 1:35 (FIG. 3).

Stability of the TOTIN-5:DNA Complex During Agarose Gel Electrophoresis

The stability of dsDNA-dye complexes to electrophoresis was examined as described by Benson, S. C., Mathies, R. A., and Glazer, A. N. (1993) *Nucleic Acids Res.* 21, 5720–5726. Measurement of the off-rate of dye during electrophoresis of complexes of λDNA-HindIII restriction fragments with TOTIN-5, performed at a ratio of 1:20 dye:DNA bp, gave a $t_{0.5}$ of 114 min.

Figure 3A:
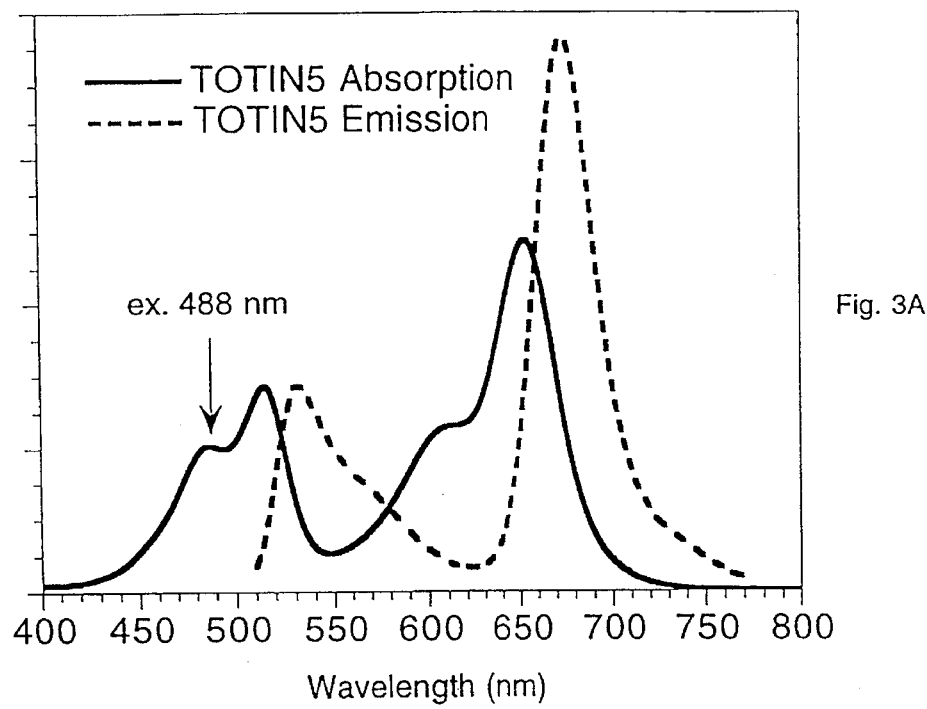
FIG. 3A is illustrates TOTIN-5 absorption and fluorescence emission spectra.
Figure 3B:
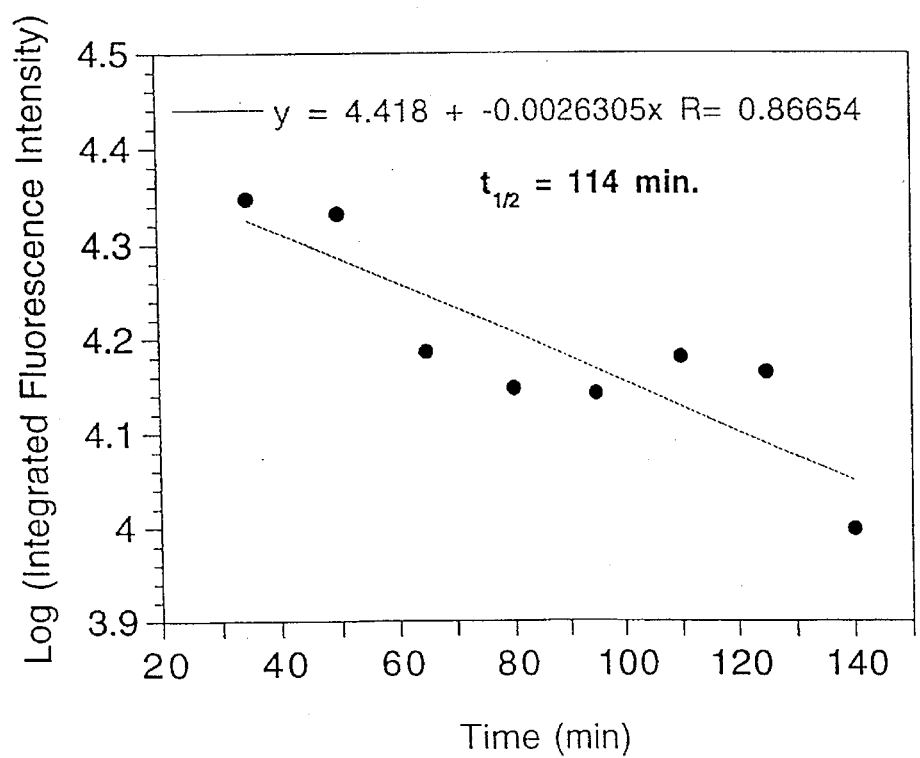
FIG. 3B is a graph of the rate of dissociation of preformed λDNA/HindIII-TOTIN-5 complexes during electrophoresis.

In FIG. 3A, the solid curve shows the absorption spectrum of TOTIN-5 (c=$6 \times 10^{-6}$M) bound to calf thymus DNA (c=$3 \times 10^{-6}$M bp) at 20 bp:dye at 4 mM TAE buffer pH 8.2. The dashed curve represents the fluorescence emission spectrum of the dye (c=$2 \times 10^{-7}$M) on excitation in 488 nm in 4 mM TAE pH 8.2, when bound to calf thymus DNA (C=$2 \times 10^{-5}$ M bp) at 100 bp:dye. All spectra were recorded at room temperature after incubation of the dyes with the DNA for 15 min. in the dark. The intensities at the $\lambda_{max}$ of the TO donor chromophore absorption (507 nm) and emission spectra (532 nm) were arbitrarily equalized.

in FIG. 3B, λDNA/HindIII fragments (4 ng; 800 pg/µl, 5 µl aliquots) complexed to TOTIN-5 at 1 dye: 20 bp in 50 mM NaCl, were loaded at consecutive 15 min. intervals and electrophoresed over 140 min. The logarithm of the integrated fluorescence intensity of the bands is plotted against electrophoresis time of the fragments. The slope of the linear fit of the data gives a $t_{0.5}$ of 114 min. for the dsDNA-TOTIN-5 complex. For other experimental details, see Benson et al. (1993), supra.

The dependence of donor and acceptor fluorescence emission of TOTIN-5 as a function of fractional saturation of binding sites in dsDNA was determined. Fluorescence emission spectra of the dye (C=$2 \times 10^{-7}$M) upon excitation at 488 nm in 4 mM TAE pH 8.2 was determined, when the dye was bound to decreasing concentrations of calf thymus DNA at various bp:dye ratios. Spectra were recorded at room temperature after incubation of the dye with the DNA for 15 min. in the dark and the fluorescence intensities were recorded at the emission maximum at 672 nm for TIN-5 and 532 nm for TO.

To obtain the absorption spectra of iodopropyl-TIN-5, pure recrystallized iodopropyl-TIN-5 (4.8 mg, mw=654) was dissolved in 50 ml MeOH to give a stock solution ($1.47 \times 10^{-4}$ M). A molar extinction coefficient of 230,200 at $\lambda_{max}$=643 nm was determined on diluted sample (1/50) in MeOH. The solvent dependence of the absorption spectrum of TIN-5 was determined by running equal aliquots of the stock solution in MeOH, 4 mM Tris-acetate-0.1 mM ethylenediamine tetraacetate buffer, pH 8.2 (TAE), or buffer plus calf thymus dsDNA at 20 base pairs (bp):dye. The following table indicates the results.

TABLE 1

Absorption data for TIN-5 and TOTIN.[1]

| Dye | Solvent | $\lambda_{max}$ nm | $\epsilon$ $M^{-1}$ $cm^{-1}$ |
|---|---|---|---|
| TOTIN-5 | MeOH | 288 | 17,900 |
|  |  | 506 | 79,000 |
|  |  | 647 | 146,400 |
|  | TAE | 289 | 15,300 |
|  |  | 508 | 69,600 |
|  |  | 649 | 126,500 |
|  | TAE/DNA | 515 | 60,000 |
|  |  | 653 | 102,300 |
| TIN-5 | MeOH | 318 | 11,500 |
|  |  | 643 | 230,200 |
|  | TAE | 318 | 9,200 |
|  |  | 639 | 172,800 |
|  | TAE/DNA | 651 | 142,600 |

[1] All spectra in MeOH and TAE (4 mM TAE buffer pH 8.2) were at room temperature with dyes at ~$3 \times 10^{-6}$M. Spectra of dyes bound to dsDNA ($3 \times 10^{-6}$M dye) were with calf thymus DNA ($6 \times 10^{-5}$M bp) at 20 bp:dye, in 4 mM TAE buffer pH 8.2, recorded at room temperature after incubation of the dyes with the DNA for 15 minutes in the dark.

The 450–550 nm region of the absorption spectrum of the TOTIN-5 heterodimer was closely matched by addition of the absorption spectra of the two monomers run at equally molar concentrations. Therefore, the molar extinction coefficient TOTIN-5 in MeOH ($\lambda_{max}$abs=507 nm, $\epsilon$=79,000) was calculated from the known extinction coefficients of TO (Benson et al. (1993), supra) and iodopropyl-TIN-5 at 507 nm. The solvent dependence of the absorption spectrum of TOTIN-5 was determined as for the TIN-5 monomer (Table 1).

It is evident from the above results that the subject composition provide a new class of dicarbocyanine dyes with high dsDNA binding affinity and particularly favorable spectroscopic properties for fluorescence detection in the far red region of the visible spectrum. The acceptor TO chromophore in TOTIN-5 is a dicarbocyanine dye which contains a non-planar, sterically bulky, gem dimethyl substituted indolenine group coupled to a planar benzothiazole by a pentamethine bridge.

TOTIN-5 is found to be superior to the best DNA-binding energy transfer dye reported, TOTAB (Benson et al. (1993) supra), which was designed for strong absorbance at 488 nm, a large Stokes shift and strong fluorescence emission. TOTAB and TOTIN-5 complexes with dsDNA, at 1 dye:20 DNA bp, have similar stabilities to agarose gel electrophoresis; $t_{0.5}$ values of 124 min. and 114 min., respectively. The two heterodimers have the same molar extinction coefficient ($\epsilon_M$) at 488 nm, but the TIN-5 chromophore in TOTIN-5 has an $\epsilon_M$ two-fold higher than the thiazole blue (TAB) chromophore of TOTAB. Evidently the fluorescence quantum yields of TOTIN-5 and TAB are near-equivalent, because on 488 nm excitation of equimolar solutions of their dsDNA complexes, the emission from TOTIN-5 is also twice as high as that from TOTAB. The TOTIN-5 dye has the further advantage that TIN-5 emission in DNA-bound TOTIN-5 is not quenched even at one dye:5 DNA bp in contrast to the strong quenching of the TAB emission of TOTAB at high saturation of dsDNA binding sites. In addition, the TOTIN-5 fluorescence emission maximum (672 nm) lies 12 nm further to the red than that of TOTAB (660 nm).

It is evident from the above results, that the subject dyes provide a new chemical class of heterodimeric dsDNA-binding dyes which exploit energy transfer. The large Stokes shift and the red emission of the subject dyes are particularly favorable because they allow efficient rejection of extraneous fluorescence in Raman scattering of water. Such dyes are valuable for high sensitivity fluorescence detection of DNA, particularly in multiplex formats.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:
1. A compound of the formula:
wherein:

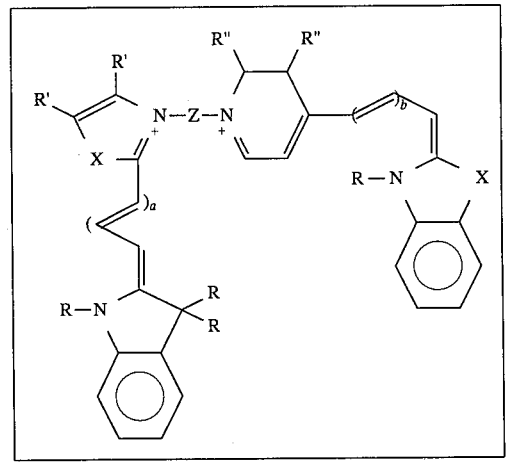

a is from 0 to 6, b is from 0 to 4;

R, R' and R" are hydrogen, hydrocarbyl, heterosubstituted hydrocarbyl or heterosubstituent of not more than 12 carbon atoms and 4 heteroatoms, with the proviso that two R's or two R"s bonded to adjacent carbon atoms may be taken together to define a ring and two R"s may be taken together to define a double bond and R is other than hydrogen;

X is sulfur, oxygen, nitrogen or selenium; and

Z is a linking group comprising hydrocarbyleneaminohydrocarbylene.

2. A compound according to claim 1, wherein a is from 1 to 5, b is from 0 to 3, R is alkyl of from 1 to 3 carbon atoms, and Z is an alkyleneaminoalkylene group, wherein alkylene is of from 2 to 4 carbon atoms.

3. A compound of the formula:

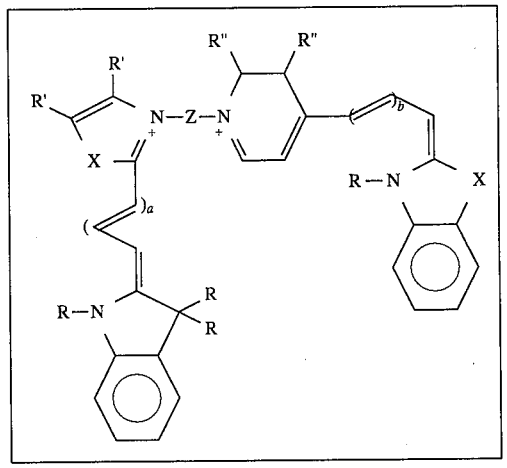

wherein:

a is from 0 to 6,:

b is from 0 to 4;

each of the R groups are the same or different, and are alkyl or substituted alkyl of from 1 to 12 carbon atoms;

each of the R' groups are the same or different, wherein when other than hydrogen are of from 1 to 12 carbon atoms and 0 to 2 heteroatoms or are taken together to form a carbocyclic ring;

each of the R" groups are the same or different, come within the definition of R', except that R"s may be taken together to define a double bond;

X is sulfur, oxygen, nitrogen or selenium; and

Z is a linking group comprising hydrocarbyleneaminohydrocarbylene.

4. A compound according to claim 3, wherein X is sulfur.

5. A compound according to claim 4, wherein R is methyl.

6. A compound according to claim 3, wherein the two R's and two R"s are taken together with the carbon atoms to which they are attached to define a fused benzene ring.

Figure 2:
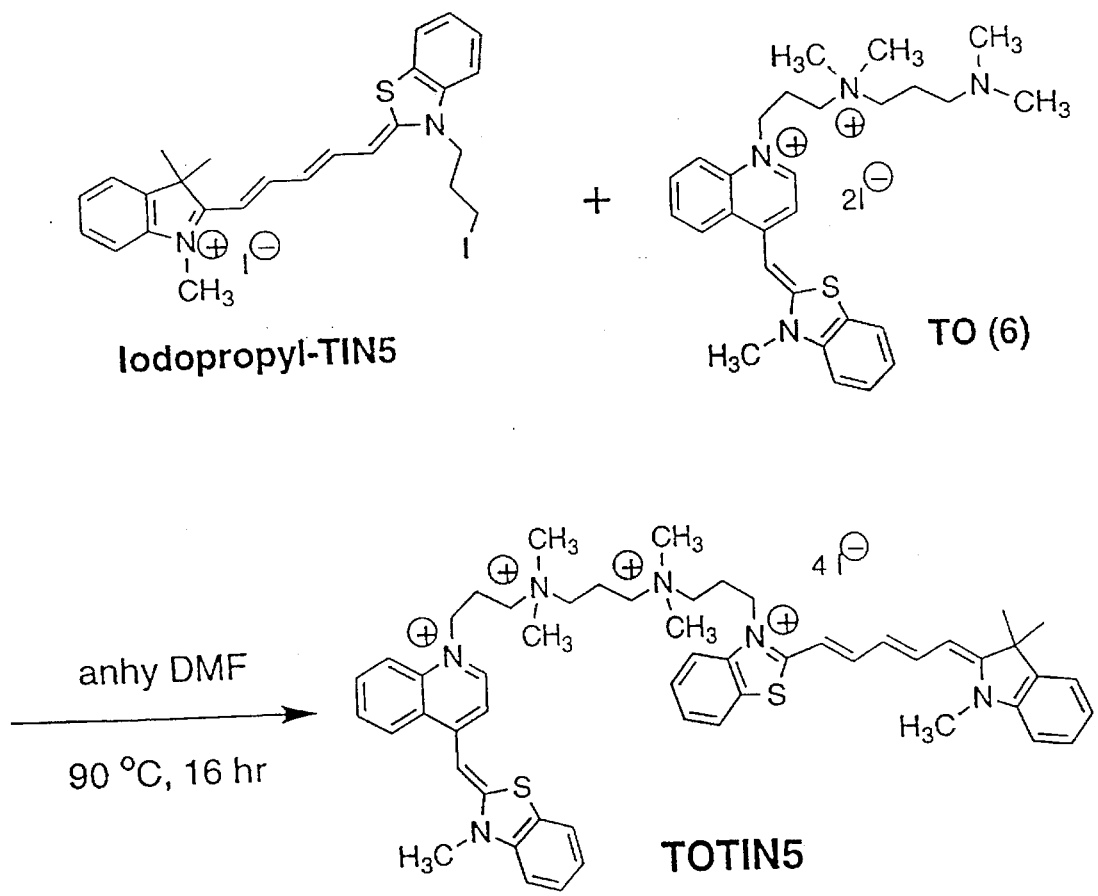
FIG. 2 (Scheme 2) is a scheme for the synthesis of TOTIN-5 heterodimer by the reaction of (tetramethylpropanediamino)propyl thiazole orange (TO6) with (TIN-5) (2-[5'-benzo-1",3"-thiazole)-2"-ylidene)-1',3'-pentadienyl]-methul-3,3-dimethylindoleniuium iodide)

7. 1-[1'-[4'-[3"-methyl-2",3"-dihydro-(benzo-1",3"-thiazole)-2"-ylidene]-methyl-quinolinium iodide]]-11-[3'-[2'-[5'-1'"-methyl-3'",3'"-dimethylindolenine-2'"-ylidene )-1",3"-[pentadien-1"-yl]-benzo-1'3'-thiazolium iodide]]-4,4,7,7-tetramethyl-4,7-diazaundecamethylene diiodide having the structure TOTIN5 of FIG. 2.

8. A dsDNA comprising a dye according to claim 1.

9. A dsDNA comprising a dye according to claim 3.

10. A dsDNA comprising a dye according to claim 7.

11. A dsDNA according to claim 8, wherein said dye is present in a ratio of one dye molecule per 4 to 200 base pairs of said dsDNA.

12. A dsDNA according to claim 8 covalently bonded to a ligand which is a member of a specific binding pair.

* * * * *

UNITED STATES PATENT AND TRADEMARK OFFICE
CERTIFICATE OF CORRECTION

PATENT NO. : 5,565,554

DATED : October 15, 1996

INVENTOR(S) : Alexander N. Glazer and Scott C. Benson

It is certified that error appears in the above-identified patent and that said Letters Patent is hereby corrected as shown below:

| | |
|---|---|
| Column 1, line 50 | delete "." after *Cytometry* 10, |
| Column 1, line 56 | "3"iodopropyl" should read --3"-iodopropyl"-- |
| Column 1, line 63 | "methul-3,3-dimethylindoleniuium" should read --methyl-3,3-dimethylindoleninium-- |
| Column 1, line 64 | "Fig. 3A is illustrates TOTIN-5 absorption and fluorescence emission spectra" should read --Fig. 3A illustrates TOTIN-5-double stranded DNA complex absorption and fluorescence emission spectra-- |
| Column 2, line 6 | "get" should read --gel-- |
| Column 3, line 30 | "usualy" should read --usually-- |
| Column 3, line 37 | "from" should read --form-- |
| Column 4, line 2 | "RΔ" should read --R"-- |
| Column 5, line 8 | "0.2°" should read --0.2-- |
| Column 5, line 34 | "basse" should read --base-- |
| Column 5, line 49 | "Trisacetate" should read --Tris-acetate-- |

UNITED STATES PATENT AND TRADEMARK OFFICE
CERTIFICATE OF CORRECTION

PATENT NO. : 5,565,554

DATED : October 15, 1996

INVENTOR(S) : Alexander N. Glazer and Scott C. Benson

It is certified that error appears in the above-identified patent and that said Letters Patent is hereby corrected as shown below:

| | |
|---|---|
| Column 7, line 44 | "*coil*" should read --*coli*-- |
| Column 8, line 7 | between "where the functionality" and "to other than a naturally occurring" insert --bonds-- |
| Column 8, line 21 | "3'proximal" should read --3' proximal-- |
| Column 9, line 10 | "3'or" should read --3' or-- |
| Column 9, lines 23-34 | "With the subject compositions one can also detect proteins to transcriptional initiation elements," should read --With the subject compositions one can also detect proteins that bind to transcriptional initiation elements,-- |
| Column 9, line 56 | "(1941)(1941)" should read --(1941)-- |
| Column 9, line 59 | "benothiazole" should read --benzothiazole-- |
| Column 10, line 26 | "2,3,3," should read --2,3,3-- |
| Column 10, line 29 | "2" should read --2-- |
| Column 10, line 30 | "AC$_2$O" should read --Ac$_2$O-- |

UNITED STATES PATENT AND TRADEMARK OFFICE
CERTIFICATE OF CORRECTION

PATENT NO.   : 5,565,554

DATED        : October 15, 1996

INVENTOR(S)  : Alexander N. Glazer and Scott C. Benson

It is certified that error appears in the above-identified patent and that said Letters Patent is hereby corrected as shown below:

Column 12, line 17    "was determined" should read --were determined--

Signed and Sealed this

Tenth Day of June, 1997

Attest:

Attesting Officer

BRUCE LEHMAN

Commissioner of Patents and Trademarks